(12) United States Patent
Fahl

(10) Patent No.: US 11,878,121 B2
(45) Date of Patent: Jan. 23, 2024

(54) HEAT AND MOISTURE EXCHANGER WITH LIPPED VALVE PLATE AND GROOVED VALVE SEAT

(71) Applicant: Andreas Fahl Medizintechnik—Vertrieb GmbH, Cologne (DE)

(72) Inventor: Andreas Fahl, Cologne (DE)

(73) Assignee: Andreas Fahl Medizintechnik—Vertrieb GmbH, Kohn (DE)

( * ) Notice: Subject to any disclaimer, the term of this patent is extended or adjusted under 35 U.S.C. 154(b) by 345 days.

(21) Appl. No.: 16/620,733

(22) PCT Filed: Dec. 19, 2018

(86) PCT No.: PCT/EP2018/085814
§ 371 (c)(1),
(2) Date: Dec. 9, 2019

(87) PCT Pub. No.: WO2019/121894
PCT Pub. Date: Jun. 27, 2019

(65) Prior Publication Data
US 2020/0139070 A1 May 7, 2020

(30) Foreign Application Priority Data
Dec. 20, 2017 (DE) .................. 10 2017 130 662.5

(51) Int. Cl.
*A61M 16/10* (2006.01)
*A61M 16/04* (2006.01)
(Continued)

(52) U.S. Cl.
CPC ......... *A61M 16/1045* (2013.01); *A61F 2/203* (2013.01); *A61M 16/0468* (2013.01);
(Continued)

(58) Field of Classification Search
CPC ............ A61M 16/0468; A61M 16/047; A61M 16/1045; A61M 16/20; A61M 16/203;
(Continued)

(56) References Cited

U.S. PATENT DOCUMENTS

| 866,906 A | * | 9/1907 | Berry | ........................ | F16K 1/42 |
| | | | | | 251/333 |
| 1,486,251 A | * | 3/1924 | Knight | ...................... | F16K 1/42 |
| | | | | | 251/333 |

(Continued)

FOREIGN PATENT DOCUMENTS

| CN | 105848702 A | 8/2016 |
| DE | 102012024817 A1 | 6/2014 |

(Continued)

OTHER PUBLICATIONS

International Search Report dated Mar. 29, 2019; International Application No. PCT/EP2018/085814.

(Continued)

*Primary Examiner* — Kathryn E Ditmer
(74) *Attorney, Agent, or Firm* — DINSMORE & SHOHL LLP

(57) ABSTRACT

A heat and moisture exchanger (IO) for tracheostomized or laryn-gectomized patients, having a valve plate and a housing, wherein: the valve plate has a radially surrounding lip, and the housing comprises a valve seat which encloses a distal opening of the housing, the valve seat has a groove for receiving the lip, the valve plate is associated with the distal opening of the housing, and the valve plate can be moved into a closed position in which the lip engages in the groove.

7 Claims, 4 Drawing Sheets

(51) Int. Cl.
*A61F 2/20* (2006.01)
*A61M 16/20* (2006.01)

(52) U.S. Cl.
CPC .......... *A61M 16/201* (2014.02); *A61F 2/20* (2013.01); *A61F 2220/0033* (2013.01); *A61F 2230/0054* (2013.01); *A61F 2250/0069* (2013.01); *A61M 16/047* (2013.01); *A61M 16/105* (2013.01); *A61M 2210/0618* (2013.01)

(58) Field of Classification Search
CPC ........ A61F 2002/206; F16K 1/36; F16K 1/42; F16K 25/00
See application file for complete search history.

(56) References Cited

U.S. PATENT DOCUMENTS

| | | | | | |
|---|---|---|---|---|---|
| 1,555,025 | A | * | 9/1925 | Raymond | F16K 1/34 251/333 |
| 1,587,080 | A | * | 6/1926 | Marcelli | F16K 41/14 251/220 |
| 1,717,022 | A | * | 6/1929 | Foulkrod | F16K 15/18 251/275 |
| 2,136,835 | A | * | 11/1938 | Begg | B60T 11/22 60/589 |
| 2,317,068 | A | * | 4/1943 | Kucki | G01F 11/263 222/309 |
| 2,414,908 | A | * | 1/1947 | Smith | F16K 1/46 251/333 |
| 2,447,510 | A | * | 8/1948 | Langdon | F16K 15/18 251/214 |
| 2,676,781 | A | * | 4/1954 | Hobbs | F16J 15/186 251/210 |
| 2,683,464 | A | * | 7/1954 | St Clair | F16K 17/0466 137/540 |
| 2,687,276 | A | * | 8/1954 | Hornsby | F16K 47/00 251/113 |
| 2,900,166 | A | * | 8/1959 | Boosman | F16K 1/46 251/175 |
| 2,976,010 | A | * | 3/1961 | Huthsing, Sr. | F16K 1/36 251/333 |
| 4,140,148 | A | * | 2/1979 | Richter | B65D 51/1644 137/240 |
| 4,188,013 | A | * | 2/1980 | Battersby | F23N 5/107 251/175 |
| 5,020,775 | A | * | 6/1991 | Iwasaki | C30B 15/00 251/215 |
| 5,469,883 | A | * | 11/1995 | Lee | G05D 7/012 137/854 |
| 5,738,095 | A | * | 4/1998 | Persson | A61F 2/20 128/201.13 |
| 8,152,134 | B2 | * | 4/2012 | Stenberg | F16K 3/267 251/121 |
| 2004/0031527 | A1 | * | 2/2004 | Stratton | F16K 1/42 137/625.37 |
| 2011/0220108 | A1 | * | 9/2011 | Persson | A61M 16/0468 128/205.29 |
| 2015/0273168 | A1 | * | 10/2015 | Fahl | A61M 16/0468 128/205.27 |
| 2017/0102091 | A1 | * | 4/2017 | Hunt | F16K 31/50 |

FOREIGN PATENT DOCUMENTS

| | | | | |
|---|---|---|---|---|
| DE | 102013018905 A1 | * | 5/2015 | ........ A61M 16/1045 |
| DE | 102014002064 B3 | | 6/2015 | |
| EP | 2236165 A1 | | 10/2010 | |
| WO | 2006118599 A1 | | 11/2006 | |
| WO | 2008132222 A2 | | 11/2008 | |
| WO | 2010060983 A1 | | 6/2010 | |

OTHER PUBLICATIONS

First official action of priority application by the German Patent and Trademark Office.

* cited by examiner

HEAT AND MOISTURE EXCHANGER WITH LIPPED VALVE PLATE AND GROOVED VALVE SEAT

CROSS-REFERENCE TO RELATED APPLICATIONS

This application is the U.S. national stage of PCT/EP2018/085814 filed Dec. 19, 2018, which claims priority of German Patent Application 10 2017 130 662.5 filed Dec. 20, 2017 of which is hereby incorporated by reference in its entirety.

FIELD OF THE INVENTION

The invention relates to a heat and moisture exchanger for tracheostomy or laryngectomy patients, comprising a valve plate and a housing.

BACKGROUND OF THE INVENTION

Heat and moisture exchangers for tracheostomy or laryngectomy patients are known in general from the prior art. WO 2010/060983 A1 describes a so-called respiration guard comprising a housing and a valve plate. There is a filter in the housing that extends distally to the valve plate. When pressure is applied to the valve plate, the filter is compressed and the valve plate is pressed against a valve seat, which is part of the housing, thus closing the respiration guard. This has the disadvantage that when closing the heat and moisture exchanger, the moisture in the filter material is squeezed out into the trachea of the user, or onto his clothing. The valve plate is also pushed sideways by a cage-like guide adjoining a filter receiver. The valve plate may tilt slightly, depending on where the pressure is applied, and become jammed. A further disadvantage is a somewhat imprecise tactile feedback when actuating the heat and moisture exchanger, which the user may find unpleasant. The valve plate disclosed therein also has radial outward projections that engage in holes in order to restrict distal movement of the valve plate so that it does not fall out. Such a heat and moisture exchanger also has the disadvantage that it is difficult to implant.

In particular, the object of the invention is to create a more user-friendly heat and moisture exchanger. Another object of the invention is to improve the sealing of the heat and moisture exchanger.

SUMMARY OF THE INVENTION

These problems are solved according to the invention by means of a heat and moisture exchanger for tracheostomy and laryngectomy patients, comprising at least a valve plate and a housing, wherein the valve plate comprises a radial circumferential lip, and wherein the housing comprises a valve seat that encircles a distal opening in the housing, wherein the valve seat comprises a groove for receiving the lip, wherein the valve plate is dedicated to the distal opening in the housing, and wherein the valve plate can be closed when the lip engages in the groove. The problems addressed by the invention are also solved by means of a method for closing a heat and moisture exchanger, wherein a valve plate is moved proximally, such that a lip on the valve plate engages in a groove in the housing. The problems addressed by the invention are also solved by means of a use of a heat and moisture exchanger for diverting an air flow.

A heat and moisture exchanger for tracheotomy or laryngectomy patients is proposed. It comprises a valve plate and a housing. The valve plate comprises a radial circumferential lip. The housing comprises a valve seat that encompasses a distal opening in the housing, and the valve seat comprises a groove for receiving the lip. The valve plate is dedicated to the distal opening in the housing, such that the valve plate can be closed when the lip engages in the groove.

With a surgical intervention in the upper respiratory tract, it may be necessary to insert an artificial tracheostoma into the trachea so that air can be inhaled directly into the lungs, circumventing the mouth and larynx. By way of example, patients who have undergone a laryngectomy, thus having had the larynx removed surgically, must keep the tracheostoma open and stable, for which reason tracheal cannulas in particular, normally comprising an outer and inner cannula, must be placed in the tracheostoma. It is also possible to use so-called "tracheostoma buttons," in particular for persons who no longer need a tracheal cannula.

So-called "shunt valves" can also be placed in the tracheostoma, which enable a restoration of the voice. Lastly, a filter system can also be inserted in the tracheostoma in both tracheotomy as well as laryngectomy patients. These filter systems are composed in particular of a bandage containing a filter in a housing, and/or filter material, or a typical self-adhesive base plate—normally made of plastic—in which filters in a housing, and/or filter materials of different types can be used.

The generic heat and moisture exchangers, also referred to as "artificial noses," are types of filter systems used for laryngo-tracheal aids such as tracheal cannulas, shunt valves, tracheostoma buttons and filter systems with a bandage or base plate. These form the regulating mechanisms for heating and moisturizing inhaled air that are lacking in laryngectomy and tracheotomy patients, such that the trachea is not brought in contact with extremely dry, cold, and unfiltered air. The irritation caused by such air results in an increased mucus production, with the consequential danger of choking. Inhaled air is moisturized, heated, and simultaneously filtered by the heat and moisture exchanger. As a result, the aforementioned choking danger is substantially avoided. It helps to wear the artificial nose on a regular basis, in particular with strong secretions, because secretion is reduced through moisturizing the mucous membrane in the trachea.

Generic heat and moisture exchangers for laryngectomy and tracheotomy patients contain a filter material—normally made of paper or foam material—through which the inhaled and exhaled air is conducted. The filter material retains moisture when exhaling, which is then transported into the trachea when inhaling. There are heat and moisture exchangers known from the prior art in a large variety of designs for various adapters. The universal adapter according to DIN EN ISO 5356-1 has a diameter of 15 mm, and other adapters with a diameter of 22 mm are also known from the prior art.

Another aid for laryngectomy patients comprises voice prostheses, which are used to recover the voice after a laryngectomy. The recovery of the voice can be achieved through surgical measures. The most important aid in this case is the voice prosthesis, also referred to as a "shunt valve." The function of the removed larynx can be replaced by a voice prosthesis. Air can be supplied from the lungs into the throat via the esophagus with a voice prosthesis. The exhaled air is then used for speaking. The voice prosthesis also seals the connection between the esophagus and the trachea when swallowing food or liquids, thus protecting the user of the voice prosthesis from inadvertently inhaling such food or liquids.

After the scars have healed following the surgical intervention, the patient is normally unable to speak. In order to enable speech, the air outlet on the throat must be closed when using a voice prosthesis or the still existing larynx in the case of tracheotomy patients, so that the air is conducted through the voice prosthesis or the larynx. For this, the heat and moisture exchanger according to the invention contains the valve plate, in order to form a valve function therein.

In one embodiment, the valve plate is designed as a cover. The valve plate is particularly preferably round. In another embodiment, the valve plate is in the form of a plate. In another embodiment, the valve plate has an at least partially curved shape. In particular, the at least partially curved shape is located on a distal side of the valve plate. It is also preferred that the proximal side of the valve plate is substantially flat, with the exception of the lip. In particular, the surface of the valve plate has a curved shape in a least one cross section, in particular on the distal side of the surface. In another embodiment, the valve plate has a recess, in particular in the distal surface of the valve plate, in particular substantially in the middle.

In another embodiment, the valve plate has an in particular concentric, circumferential curvature, in particular on the distal side. The curvature is preferably annular. A concentric curvature on the distal surface of the valve plate has a curvature radius of approx. 10 mm to approx. 20 mm in one embodiment, in a cross section extending from the distal side to the proximal side, more preferably approx. 12 mm to approx. 16 mm, more preferably approx. 13 mm to approx. 15 mm, more preferably approx. 14 mm, more preferably approx. 14.14 mm. In another embodiment there is a recess of approx. 30 mm to approx. 50 mm in a cross section extending from the distal side to the proximal side, more preferably approx. 35 mm to approx. 45 mm, more preferably approx. 40 mm. The curvature preferably surrounds the recess. In another embodiment the proximal side, lying opposite the curvature and recess, is substantially flat. The recess inside the annular curvature is preferably circular.

When the term "approx." is used in the framework of the invention in conjunction with values or value ranges, a tolerance range is to be understood that is regarded as typical by the person skilled in the art in this field, in particular a tolerance range of ±20%, preferably ±10%, more preferably ±5%.

In another preferred embodiment, the valve plate is airtight. The valve plate preferably has no holes enabling gas or air to pass through the valve plate. In another embodiment, the valve plate has a radial circumferential lip, which preferably extends proximally. The lip extends proximally in one embodiment from a proximal surface of the valve plate approx. 0.5 mm to approx. 1.5 mm, more preferably approx. 0.5 mm to approx. 1 mm, more preferably approx. 0.7 mm. It is also preferred that the lip is dedicated to an edge of the valve plate. In another embodiment, the valve plate is materially bonded. In another embodiment, the lip is injection molded onto the valve plate. In one embodiment, the lip comprises an elastic material, e.g. medical silicone or rubber in particular. It can preferably be produced in a 2-component injection molding process with the actual valve plate, which is made of a harder material than the lip. In another embodiment the lip comprises a rigid material, e.g. a material selected from the group comprising polyamide, polycarbonate, acrylonitrile butadiene styrene (ABS), and/or a mixture of at least two of these materials. In another embodiment, the lip comprises the same material as the valve plate.

The lip is a material extension, in particular, that preferably extends in the proximal direction from a substantially planar surface of the valve plate. The lip is preferably circumferential in the radial direction, in particular such that it encircles the valve plate entirely. The lip is also preferably dedicated to an outer edge of the valve plate, in particular such that the lip forms the outer edge of the valve plate. In another embodiment, the lip has a substantially rectangular cross section. In another embodiment, the lip has a substantially trapezoidal shape.

The directional terms used in the framework of the invention are to be understood according to the invention in reference to the intended insertion in a tracheal cannula or a tracheostoma bandage, or in reference to the body of the user. The term "distal" is understood as set forth in the present invention in reference to a feature of the device according to the invention, a placement or use thereof at a distance to, or facing away from, or lying opposite a tracheostoma bandage or a tracheal cannula, or in general the surface of the skin of a user, who wears in particular such attachment means for the device according to the invention. The term "proximal" is understood as set forth in the present invention in reference to a feature of the device according to the invention, a placement or use thereof, close to, or facing, or adjacent to a tracheostoma bandage or a tracheal cannula, or in general the surface of the skin of a user, who wears in particular such an attachment means for the device according to the invention. By way of example, a closure that is distal to the filter material means that when switching the valve plate from an open setting to a closed setting, the filter material is entirely located on the side of the valve plate facing the body of the user, i.e. the proximal side.

When the term "substantially" is used in the framework of the invention, this refers to an acceptable tolerance range for the person skilled in the art from economical and technological perspectives, such that the feature in question can still be recognized or implemented as such.

In one embodiment the housing comprises at least one filer receiver. In one embodiment, the housing is at least partially cylindrical. The housing comprises a housing wall in one embodiment. The filter receiver preferably comprises the housing wall. The housing wall is also preferably substantially cylindrical. The housing wall preferably comprises a distal and a proximal end surface, which are also preferably flat. A respiration guard is preferably dedicated to the proximal side of the housing wall. In another embodiment, the distal side of the housing wall, in particular the distal end surface, has a dedicated rim. The rim preferably extends radially away from the housing wall over its entire circumference. In particular, a distal surface of the rim is on the same plane as the distal end surface of he housing wall. In another embodiment the housing comprises a frame, preferably located distal to the filter receiver. It can also be at least partially at the same level as the filter material, and the upper surface thereof is substantially in the same plane as a distal surface of the filter material. In another preferred embodiment there are struts between the frame and filter receiver, forming a spacer between the frame and the filter receiver. The frame is preferably annular. The frame also preferably has an outer diameter that basically corresponds to an outer diameter of the filter receiver. In another embodiment, the frame has an inner diameter that is greater than an outer diameter of the valve plate. The valve plate is preferably not retained by the frame, or restricted in terms of its transverse movement in particular. The advantage of the frame is that an accidental actuation of the valve plate, for example, in particular an unintended closing of the heat and moisture exchanger by clothing, for example, can be prevented. In particular, the struts are placed such that ventilation can take place between the struts. In one embodiment, there are at least three, more preferably three to five struts.

The filter receiver is preferably substantially cylindrical, wherein it has at least one distal opening, and preferably also has at least one proximal opening. A shell on the filter receiver is also preferably gas-impermeable, and has no holes. In another preferred embodiment, the filter receiver has a respiration guard. The respiration guard is preferably dedicated to the proximal opening in the filter receiver. In one embodiment, the respiration guard comprises a grid, a screen, one or more slats, a perforated plate, and/or one or more struts, in particular arranged in a cross. In one embodiment, the respiration guard is in the shape of a star. The respiration guard is designed in particular such that it retains the filter material, so that it is not accidentally inhaled by the user of the heat and moisture exchanger.

A closed setting of the heat and moisture exchanger is understood in the framework of the present invention to mean a position of the valve plate in which the preferably circumferential lip on the valve plate engages in the groove in the valve seat, and bears in particular on the base of the groove. The closed setting is also distinguished in that a distal opening of the housing, in particular a distal opening of the filter receiver, is substantially airtight.

The housing comprises the valve seat according to the invention. The valve seat encompasses the distal opening of the housing, and is preferably designed such that the distal opening of the housing, in particular the filter receiver, can be closed by means of the valve plate such that it is substantially airtight. The groove for receiving the lip is preferably entirely circumferential. The groove preferably also opens distally. In another embodiment, the groove for receiving the lip is preferably an elongated, preferably angled recess in the material of the valve seat. The groove, or the valve seat, is preferably designed such that when closing the heat and moisture exchanger, the lip engages in the groove. In one embodiment, the valve plate, in particular a part of the proximal surface of the valve plate, bears on the valve seat, in particular on the distal end surface of the housing wall and/or the distal surface of the rim when the heat and moisture exchanger is closed. In another embodiment, the lip engages in the groove, in particular when closed, such that the proximal surface of the valve plate does not bear on the valve seat, and in particular, the valve plate does not lie on a distal end surface of the filter receiver or a distal surface of the rim, because the lip extends proximally further from the valve plate than the depth of the groove. This means that the heat and moisture exchanger is closed by the engagement of the lip in the groove, before a part of the proximal surface of the valve plate bears on the valve seat, in particular on a distal end surface of the filter receiver or the distal surface of the rim. In one embodiment, the depth of the groove is approx. 0.1 mm to approx. 0.5 mm, preferably 0.2 mm to 0.3 mm, more preferably approx. 0.2 mm. In another embodiment, the groove of the valve seat has a depth of approx. 10% to approx. 90%, more preferably approx. 80% to approx. 90%, more preferably approx. 85% to approx. 90%, of the proximal extension of the lip. In another embodiment, the groove has a width of approx. 1.1 to 2 times, preferably approx. 1.5 times the width of the lip. As set forth in the invention, the depth of the groove is understood to be the extension of the groove from a distal end surface of the housing, in particular the filter receiver, and/or the distal surface of the rim, to a base of the groove.

The base of the groove is characterized in particular by the substantially deepest point of the groove, which is flat in one embodiment. In another embodiment, the base of the groove comprises the section of the groove on which the lip bears.

The advantage of the sealing by means of the lip that engages in a groove is that the user receives a tactile feedback when closing the heat and moisture exchanger when the lip engages in the groove, or when the valve is closed. Furthermore, the sealing effect is increased by the labyrinthine seal of the groove and the lip. Another advantage of the seal in the proposed sealing of the heat and moisture exchanger is that when closing the valve plate, it becomes centered by the engagement of the lip in the groove, thus ensuring a secure seating of the valve plate on the valve seat.

In another embodiment, the groove has a U-shaped, V-shaped, square or trapezoidal cross section. In particular, a trapezoidal groove comprises a distally expanding cross section. The material of the valve seat encompassing the groove is preferably substantially flat. In particular, the groove is an elongated, in particular angled recess in the a substantially flat surface of the material.

In another embodiment, the valve seat has a rim that encircles the housing. In particular, the rim encircles the filter receiver. In another embodiment, the rim has a radially outward extending material accumulation, which preferably has a substantially flat distal surface. The rim is also preferably located on the distal end of the filter receiver. A distal surface of the rim also preferably borders directly on a distal end surface of the filter receiver, and preferably forms a substantially flat surface therewith, in which the groove is located. The valve seat also preferably comprises the distal surface of the rim and the distal end surface of the filter receiver. The groove is preferably located in the distal surface of the rim and/or the distal end surface of the filter receiver. Because of the rim, a bearing surface of the valve plate in one embodiment is greater than when the valve plate only bears on the end surface of the filter seat. The rim also advantageously allows for an adjustment of the radius of the groove and/or the width of the groove to a radius of the valve plate and/or a width of the lip. Another advantage of the rim is a robust configuration of the struts, which retain the frame of the housing in particular. The struts are preferably located on the rim and/or the distal end surface of the filter receiver. Inward and outward are understood in particular to mean directions starting from the housing wall.

In another embodiment, the housing has a pin receiver. In particular, the pin receiver is in the filter receiver, preferably in the middle of the filter receiver. Particularly preferably, the pin receiver extends distally to the height of an edge of the housing, in particular to the height of the distal end surface of the filter receiver, or the housing wall. In another embodiment, the pin receiver has a height from the proximal end to the distal end that is less than the height of the housing wall, in particular the filter receiver. The pin receiver is preferably located on the respiration guard. In particular, the pin receiver is located in the housing, distally to the respiration guard. In another embodiment, the pin receiver is materially bonded to the respiration guard. In another embodiment, at least parts of the respiration guard extend radially, at least partially, toward the housing wall, starting from the pin receiver. The respiration guard is preferably in the shape of a cross, with the pin receiver in the center. The cross can have three arms or four. In another embodiment, the cross can have any number of arms, in particular more than four.

In another embodiment, the pin receiver has a receiver for a latch. In particular, the pin receiver is at least partially in the form of a latch receiver, more preferably as at least one spring-loaded functional element of a snap-fit connection. It is also preferred that the pin receiver has two to five, more preferably three to four latch receivers. The latch receivers are preferably elastic, in particular substantially spring-loaded. A resilient part of the snap-fit connection is preferably formed by the latch receiver.

A snap-fit connection is generally understood to be a connection of at least two functional elements that are joined together. At least one of the functional elements becomes deformed in a spring-loaded or elastic manner, and hooks onto the second functional element in a releasable or non-releasable manner. By way of example, the pin receiver comprises two to five, preferably four latch receivers in the form of spring-loaded functional elements, which have a recess. The pin also preferably has a circumferential latching projection. When the pin is joined in the pin receiver, the latch receivers are bent by the pin in an elastic manner, until the latching projection engages behind the recess, and snaps into the latch receivers. The pin receiver and the pin preferably form a form fitting connection.

In another embodiment, the valve plate comprises a pin. In a preferred embodiment, the valve plate comprises a pin that can be inserted into the pin receiver of the housing, in particular in a transverse direction. In particular, the pin forms a substantially rigid element of the snap-fit connection in one embodiment. The pin receiver is also preferably designed such that the valve plate can be moved in a transverse direction from the proximal toward the lateral position and back. In particular, the valve plate can move transversely approx. 6 mm to approx. 9 mm, preferably approx. 6 mm to approx. 7 mm, in relation to the housing. Preferably, the proximal movement of the valve plate is also delimited by a distal extension of the pin receiver. In particular, the proximal movement of the valve plate is restricted by placing the valve plate on the pin receiver. In another embodiment, a distal movement is delimited by the form fitting connection of the latching projection and the latch receiver, or the pin and the pin receiver, in particular by the snap-fit connection. In one embodiment, a restriction of the proximal movement of the valve plate is preferably delimited by the engagement of the lip in the groove, or by placing the lip against the base of the groove. In another embodiment, a distal movement of the valve plate is delimited in that it is substantially at the same height as the frame. In another embodiment, the pin receiver is located in the middle of the filter receiver of the housing.

In another advantageous embodiment, the heat and moisture exchanger comprises a spring element dedicated to the valve plate. The spring element is preferably located such that it exerts a return force on the valve plate when the valve plate is moved proximally by means of a closing force. In particular, the spring element moves the valve plate to an open position after the closing force has been removed.

In another embodiment, the spring element comprises a central ring for receiving the pin. The ring preferably ensures that the return force exerted on the valve plate by the spring element is substantially even and preferably acts on the middle of the valve plate, in particular in order to prevent a tilting of the valve plate when it is returned to the open position.

In another preferred embodiment, the spring element comprises two to eight, more preferably two to four, more preferably precisely four, spring struts, extending in particular from the central ring. The spring struts are preferably in the form of leaf springs. In another embodiment, the at least two spring struts have a T-shaped design. In particular, the T-shaped spring struts are formed by a radial stem and a crosspiece at a substantially right angle thereto. The spring struts in the form of leaf springs substantially extend only in the radial direction, and do not have crosspieces. A least two of the spring struts, in particular leaf-shaped spring struts, also preferably have a curvature, extending proximally, or preferably distally, when in the assembled state. In particular in one embodiment, the crosspieces of the T-shaped spring struts are bowed proximally, or preferably distally. In another embodiment, the stems of the T-shaped spring struts are curved distally. In another embodiment, the stems of the T-shaped spring struts are curved proximally. In another embodiment, the stems of the T-shaped spring struts are not curved. In one embodiment, the crosspieces have a proximal bowing. It is particularly preferred that two T-shaped spring struts are at a right angle to two spring struts in the form of leaf springs. The spring struts are also preferably distributed on the circumference of the central ring, alternating between leaf springs and T-shaped springs. In another embodiment, the spring element comprises four leaf spring struts, which are curved distally in particular. In another embodiment, there are no T-shaped spring struts, only leaf-shaped spring struts. As set forth in the invention, a crosspiece of the T-shaped spring struts corresponds visually to the crosspiece of the letter T. The stem of the T-shaped spring strut also preferably comprises the section extending from the ring to the crosspiece.

In another preferred embodiment, there is a filter material in the filter receiver. The filter material can comprise at least one foam material. The filter material is particularly preferably substantially flush with the distal end surface of the filter receiver. In another embodiment, the filter material is substantially flush with the distal extension of the pin receiver. The filter material is particularly preferably a foam cylinder, which has a central opening for receiving the pin receiver. In another preferred embodiment, the radius of the filter material basically corresponds to the inner radius of the filter receiver. In another embodiment, the filter material is inserted in a press fit into the filter receiver.

In one embodiment, the spring element bears on the filter material. In another embodiment, the spring element bears on the pin receiver. In particular, the central ring of the spring element bears on the pin receiver. In this embodiment, the spring element does not bear, or only insubstantially bears, on the filter, and an indirect squeezing thereof is prevented when closing the heat and moisture exchanger. The spring struts preferably extend from the pin receiver and/or the filter material toward the valve plate. In one embodiment, the T-shaped spring struts bear on the filter material, preferably stabilizing the spring elements.

In another embodiment, the filter material extends over a distal edge of the filter receiver. In another embodiment, the filter material extends to the valve plate when the valve plate, or the heat and moisture exchanger, is open. In another embodiment, the filter material is created such that a return force is exerted on the valve plate by the filter material. In another embodiment, both the filter element and a spring element preferably exert a return force on the valve plate. In another embodiment, there are no spring elements. In one embodiment, the filter material is such that it can exert, in particular alone, i.e. without any spring elements, a return force on the valve plate, thus assuming the function of a spring. In another embodiment, the valve plate is attached to the filter material, in particular through adhesive or welding. This embodiment is used in particular when the pin receiver, in conjunction with the pin, does not retain the valve plate, or does not delimit the distal movement thereof. The valve plate can also be glued or welded to the filter material, if the heat and moisture exchanger does not have a pin receiver and/or pin. The disadvantage with adhesive, however, is that by applying adhesive, it penetrates the filter material, and restricts the absorption capacity of the filter material, in particular for liquids. A preferred embodiment of the heat and moisture exchanger without a spring element contains the pin receiver and the pin on the valve plate that is located therein. This embodiment ensures a defined transverse guidance when closing and opening the heat and moisture exchanger. In addition, the pin connection acts as a safeguard against losing the valve plate, without compromising the filter capacity of the filter material.

The valve plate preferably comprises a material selected from a group comprising polyamide, polycarbonate, polyoxymethylene, also referred to as polyacetal resin, preferably Delrin® 500P NC010—POM polymers from DuPont engineering, acrylonitrile butadiene styrene copolymers (ABS), and/or a mixture of at least two of these materials. In particular, the surface quality of the material, in particular the distal surface of the valve plate, exhibits a fine particle and/or homogenous morphology. The surface of the valve plate also exhibits a limited gloss.

The housing preferably comprises a material selected from the group comprising polyamide, polycarbonate, polypropylene, preferably a polypropylene copolymer, preferably Bormed™ RF825MO from Borealis AG, acrylonitrile butadiene styrene copolymers (ABS), and/or a mixture of at least two of these materials. In particular, the surface quality of housing material, in particular the surface of the ring, the struts, and/or the filter receiver, exhibit a fine particle and/or homogenous morphology. The surface of the housing also exhibits a limited gloss.

The spring element preferably contains an elastic material. In particular, the material of the spring element exhibits linear elastic properties, at least in part. In particular, this can be formed by polystyrene, polycarbonate, thermosetting plastic, in particular polyacetal, in particular a semi-crystalline thermoplastic resin with an alternating structure comprising carbon monoxide and olefin, preferably Poketone™ M 930A from Hyosung, and/or a metallic substance. Other materials with sufficient elasticity can also be used. The spring element particularly preferably has a uniform thickness. The thickness can be reduced in another embodiment, in particular in the region of a transition, e.g. a transition between the ring and the spring struts. The filter material in another embodiment comprises a material selected from a group comprising at least one open-celled foam, a tissue material, and/or paper.

In another exemplary embodiment, the heat and moisture exchanger comprises the valve plate, a spring element, and a housing, and preferably a filter material that can be placed in the housing. The valve plate has a distal upper surface and a proximal lower surface. The valve plate is encircled by a lip on the lower surface that extends toward the housing, or proximally. The valve plate also comprises a pin, which likewise extends proximally in the assembled state. The pin can be received in the pin receiver on the housing. The pin receiver preferably comprises a latch receiver preferably comprised of four segments. In conjunction with the latching projection of the pin, a recess prevents the valve plate from slipping or falling out of the pin receiver. This distal extension of the valve seat, or the filter receiver, is preferably located at the height of the maximum distal extension of the pin receiver.

The spring element preferably lies substantially on the pin receiver, but it can also be designed such that it bears on the filter material. The spring element has a central ring, in particular, which has a slot for assembly purposes, so that the ring encompasses the pin. The pin on the valve plate extends through the ring into the pin receiver. The spring element has two spring struts in this embodiment, that are curved distally in the form of a leaf spring. The spring struts lie opposite one another on the ring. There are two further T-shaped spring struts on the ring at a right angle to the other spring struts. The crosspieces of the T-shaped spring struts, which form the cross at the top of the letter T in particular, are preferably also curved distally. When the valve plate is actuated, and moved in the proximal direction, the spring struts are bent in the proximal direction, wherein they then exert a return force on the valve plate. A closing force in the proximal direction can close the valve plate, wherein the lip engages in the groove. A return force is preferably exerted on the valve plate by the spring elements that are bent by the closing of the valve plate, which then moves the valve plate to the open position when the closure force is removed or relieved.

In another exemplary embodiment, the heat and moisture exchanger comprises the valve plate and a housing, and preferably a filter material that can be placed in the housing. The valve plate comprises a distal upper surface and a proximal lower surface. The valve plate has a circumferential lip, which extends toward the housing, or in the proximal direction. The filter material extends distally over a distal end surface of the filter receiver, up to the valve plate, when it is open. The valve plate also has no pin and the housing does not have a pin receiver in this embodiment. The valve plate can be connected to the filter material with adhesive, or through welding. In another embodiment, the valve plate can be retained by the housing, in particular the frame. By way of example, the valve plate comprises stop elements, that engage beneath the frame on the proximal side.

In a third exemplary embodiment, the heat and moisture exchanger comprises the valve plate and a housing, and preferably a filter material that can be placed in the housing. The valve plate has a distal upper surface and a proximal lower surface. The valve plate has a circumferential lip on the lower surface that extends toward the housing, or proximally. The valve plate also comprises a pin that likewise extends proximally in the assembled state. The pin can be received in the pin receiver in the housing. The pin receiver preferably comprises a latch receiver, preferably composed of four segments. A recess, in conjunction with the latching projection of the pin, prevents the valve plate from slipping or falling out of the pin receiver. The distal extension of the valve seat, or the filter receiver, is preferably located at the height of the maximum distal extension of the pin receiver. The filter material extends distally beyond a distal end surface of the filter receiver, as far as the valve plate when it is open. There is no spring element.

In all of the exemplary embodiments, the surface of the upper side of the valve plate can have a recess in the proximal direction. In particular, the recess is such that a human fingertip fits comfortably in it, thus guiding it into position. In particular, a concentric curvature in the distal direction is substantially located at the height of a maximum distal extension of the distal side of the frame. The curvature in the distal direction has a cross section radius of preferably approx. 14.1 mm. The curvature in the proximal direction has a cross section radius of preferably approx. 40 mm. The curvature and the recess are preferably concentric. When open, the valve plate is preferably located substantially at the height of the frame. It is also preferred that the proximal surface of the valve plate is substantially located at the height of a proximal end surface of the frame, in order to advantageously obtain the largest possible air passage.

In all of the exemplary embodiments, the housing comprises a valve seat that comprises a groove. The groove can preferably at least partially accommodate the lip on the valve plate. Furthermore, the shape of the valve seat is such that it contains the rim encircling the housing radially on the outside, and borders in particular on a distal end surface of the filter receiver. The housing preferably also comprises struts that extend distally from the filter receiver, or the rim, and retain the frame, which can prevent an accidental actuation of the valve plate. The height of the frame from the proximal end to the distal end corresponds in particular to a maximum height of the valve plate. In another embodiment, the frame has a height from the proximal end to the distal end that corresponds to a minimum height of the valve plate. An air flow into and out of the heat and moisture exchanger takes place substantially through ventilation holes in the assembled state, which are located between the struts, the frame, and the valve seat. In particular, two struts, a section of the frame, and a section of the valve seat encompass each ventilation hole. The proximal end of the housing comprises a respiration guard that prevents the filter material from entering the body of the user of the heat and moisture exchanger, in particular preventing the user from inhaling it. Moreover, the respiration guard contains the pin receiver in the middle of the filter receiver in one embodiment, if there is a pin receiver.

In the second and third exemplary embodiment, the heat and moisture exchanger does not have a spring element. Instead, a return force can be exerted on the valve plate by the filter material. In this embodiment, a return force is generated by the deformation of the filter material when a closing force is applied. The filter material extends over the distal edge of the filter receiver, and reaches the valve plate when it is open if the heat and moisture exchanger has not been actuated. In one embodiment, the valve plate is protected against loss by the pin and the pin receiver, as described above. In another embodiment, in particular when the heat and moisture exchanger does not have a pin and/or pin receiver, the valve plate is glued to the filter material. In another embodiment, the valve plate is welded to the filter material. In another embodiment, the valve plate comprises projections that project radially outward and engage in the ventilation holes, thus restricting the distal movement of the valve plate. Other types of securing mechanisms can also be used to prevent loss.

It is preferably provided in an exemplary embodiment that the encircling lip is spaced distally apart from the groove when the heat and moisture exchanger is open. The groove is located in the radially outward extending rim of the valve seat, and has a depth of approx. 0.1 mm to approx. 0.3 mm, preferably approx. 0.2 mm. The lip, in turn, extends proximally approx. 0.5 mm to approx. 0.9 mm, preferably 0.7 mm, starting from the lower surface of the valve plate.

Furthermore, a method is proposed for closing a heat and moisture exchanger as described above, wherein a valve plate is moved proximally, wherein a lip on the valve plate engages in a groove in a housing. With this method, an airtight closure of the distal opening of the housing, or the filter receiver, can be generated. The lip on the valve plate preferably engages in the groove such that the valve plate is centered in relation to the housing. It is also advantageously provided that there is a tactile feedback as a result of the engagement of the lip in the groove, that indicates to the user that the heat and moisture exchanger is closed.

In another embodiment, the valve plate is moved proximally, counter to a return force exerted by a spring element. Advantageously, the return force, or a spring force of the spring element, is set such that the spring moves the valve plate back into the open position when the closure force in the proximal direction is removed, or is less than the return force.

In another embodiment, the valve plate is moved proximally, counter to a return force exerted by a filter material. Advantageously, the filter material is such that it exerts the return force such that the valve plate is moved back to an open position when the proximal closure force is removed or is lower than the return force. Furthermore, the valve plate is advantageously guided by the pin connection during the transverse movement to the open position and the closed position.

DESCRIPTION OF THE DRAWINGS

Furthermore, the use of a heat and moisture exchanger for redirecting an air flow is proposed. Moreover, the use of a heat and moisture exchanger for blocking an air flow is also proposed. The heat and moisture exchanger can enable a person who has had a tracheotomy or laryngectomy to guide exhaled air through a shunt or the larynx. In another embodiment, the heat and moisture exchanger described above is used for a tactile feedback when the valve plate is closed.

Further advantageous embodiments can be derived from the following drawings. The developments depicted therein are not to be interpreted as delimiting, and instead, the features described in reference thereto can be combined with one another and with the features described above to obtain further embodiments. It should also be noted that the reference symbols used in the descriptions of the drawings do not delimit the scope of protection for the present invention, but instead refer merely to the exemplary embodiments shown in the figures. Identical components or components with identical functions have the same reference symbols in the following. Therein.

DETAILED DESCRIPTION OF THE INVENTION

Figure 1:
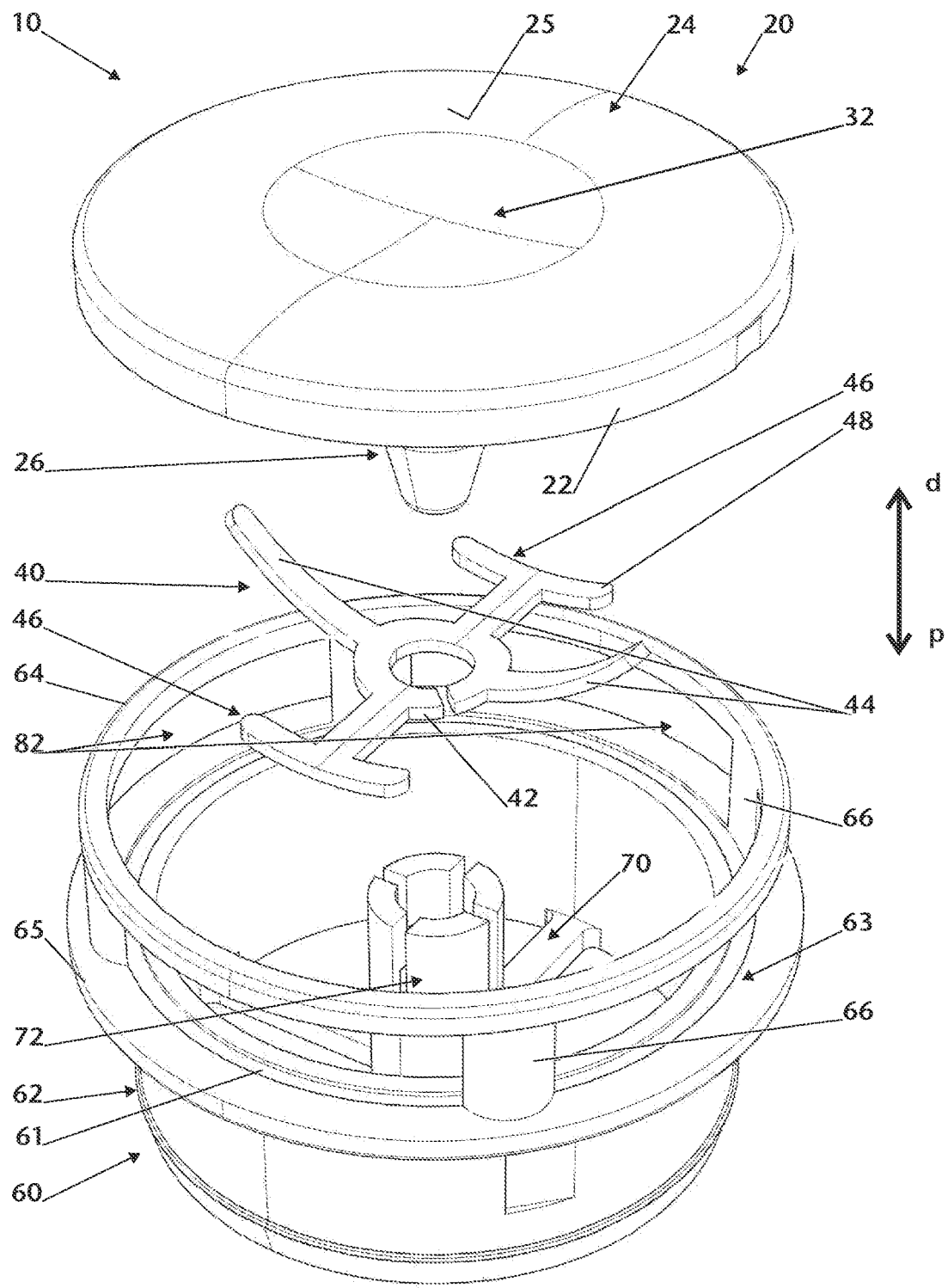
FIG. 1 shows a heat and moisture exchanger in an exploded view.

FIG. 1 shows a heat and moisture exchanger 10 in an exploded view. The heat and moisture exchanger 10 comprises a valve plate 20, a spring element 40, and a housing 60. For purposes of clarity, a filter material 50 that can be placed in the housing 60 is not shown in FIG. 1. The valve plate 20 comprises an upper surface 24, and a lower surface 30, shown in FIG. 2. The valve plate 20 is encircled by a lip 22 that extends toward the housing 60, or proximally p. Furthermore, the valve plate 20 comprises a pin 26, that likewise extends proximally p in the assembled state. The pin 26 can be received in the pin receiver 72 in the housing 60. The surface 25 of the distal upper surface 24 of the valve plate 20 has a proximal curvature 32. In particular, the curvature 32 can comfortably accommodate a human fingertip.

The housing 60 has a valve seat 63, which comprises a groove 61. The groove 61 can at least partially accommodate the lip 22 on the valve plate 20. Moreover, the shape of the valve seat 63 has a rim 65 encircling the housing 60 that faces radially outward. In particular, it can be derived from FIG. 1 that the valve seat 63 is located distally d on a filter receiver 62. The housing 60 also comprises struts 66 that extend distally d from the filter receiver, and retain a frame 64 that can prevent an accidental actuation of the valve plate 20. An airflow into and out of the heat and moisture exchanger flows substantially through the ventilation holes 82 in the assembled state, which are located between the struts 66, the frame 64, and the valve seat 63. The proximal end of the housing 60 comprises a respiration guard 70 that prevents the filter material 50, not shown in FIG. 1, from entering the body of the user of the heat and moisture exchanger 10. The respiration guard 70 contains the pin receiver 72 in the center of the filter receiver 62. There is also a spring element 40 in the heat and moisture exchanger 10 that bears substantially on the pin receiver 72 when the heat and moisture exchanger 10 is in the assembled state. The spring element 40 has a central ring 42, that contains a slot for assembly purposes, which is not further indicated therein. The pin 26 on the valve plate 20 extends through the ring 42 into the pin receiver 72 when in the assembled state. The spring element 40 has two spring struts 44 in the embodiment shown here, that are curved in the distal direction in the form of a leaf spring. The spring struts 44 lie opposite one another on the ring 42. T-shaped spring struts 46 are located on the ring 42 at a right angle to the other spring struts 44. As can also be derived from FIG. 1, the crosspieces 48 (which form the cross on the letter T) of the T-shaped spring struts 46 are likewise curved in the distal direction. When the valve plate 20 is actuated and moved proximally p, at least the spring struts 44 are curved in the proximal direction p, wherein they exert a return force 14 on the valve plate 20, indicated in FIG. 3.

Figure 2:
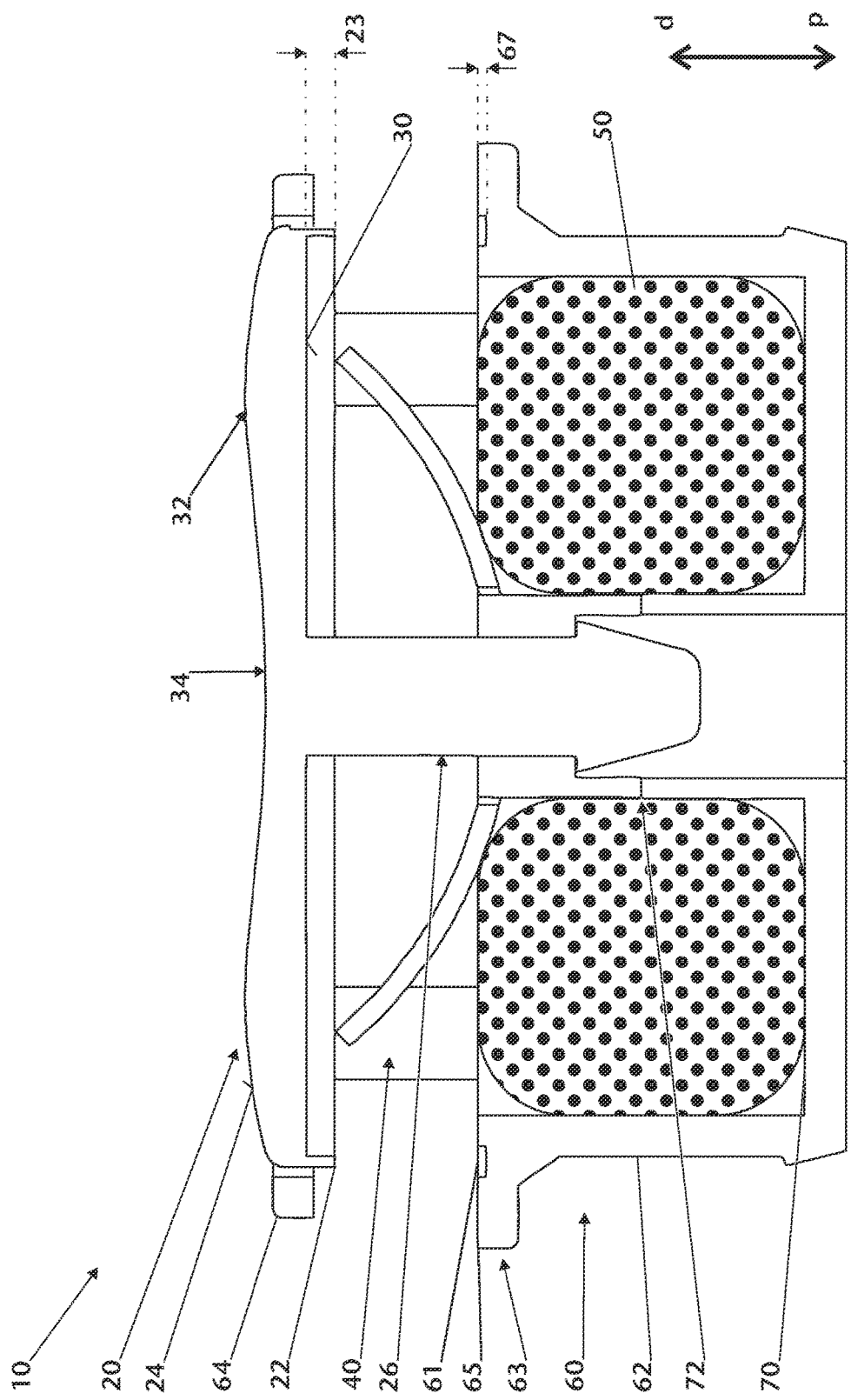
FIG. 2 shows a sectional view of the assembled heat and moisture exchanger shown in FIG. 1, in the open position.

FIG. 2 shows a sectional view of the heat and moisture exchanger 10 in the open position. The valve plate 20 can be seen therein, the pin 26 of which extends into the pin receiver 62 in the housing 60. The circumferential lip 22 can also be seen therein, which is located at a distance to the groove 61 in the distal direction d. The groove 61 is located in the radially outward extending rim 65 of the valve seat 63, and has a depth 67 of approx. 0.5 mm to approx. 1.5 mm. The lip 22 extends approx. 0.5 mm to approx. 1.5 mm, starting from the lower surface 30 of the valve plate 20 in the proximal direction p.

It can also be derived from FIG. 2 that the frame 64 is substantially located at the height of the valve plate 20. It can be seen in particular that a distally d extending concentric curvature 34 has a maximum distal extension corresponding to the height of the distal side of the frame 64. The proximal p extending, concentric circumferential curvature 34 on the surface 24 can also be seen therein. The distal curvature 34 has a cross section radius of approx. 14.1 mm. The proximal curvature 32 has a cross section radius of approx. 40 mm. It can also be seen in FIG. 2 that the distal extension of the valve seat 63, or a filter receiver 62, is basically at the height of the maximum distal extension of the pin receiver 72. A filter material 50 is located in the filter receiver 62, and extends from the respiration guard 70 to the distal edge of the valve seat 63.

Figure 3:
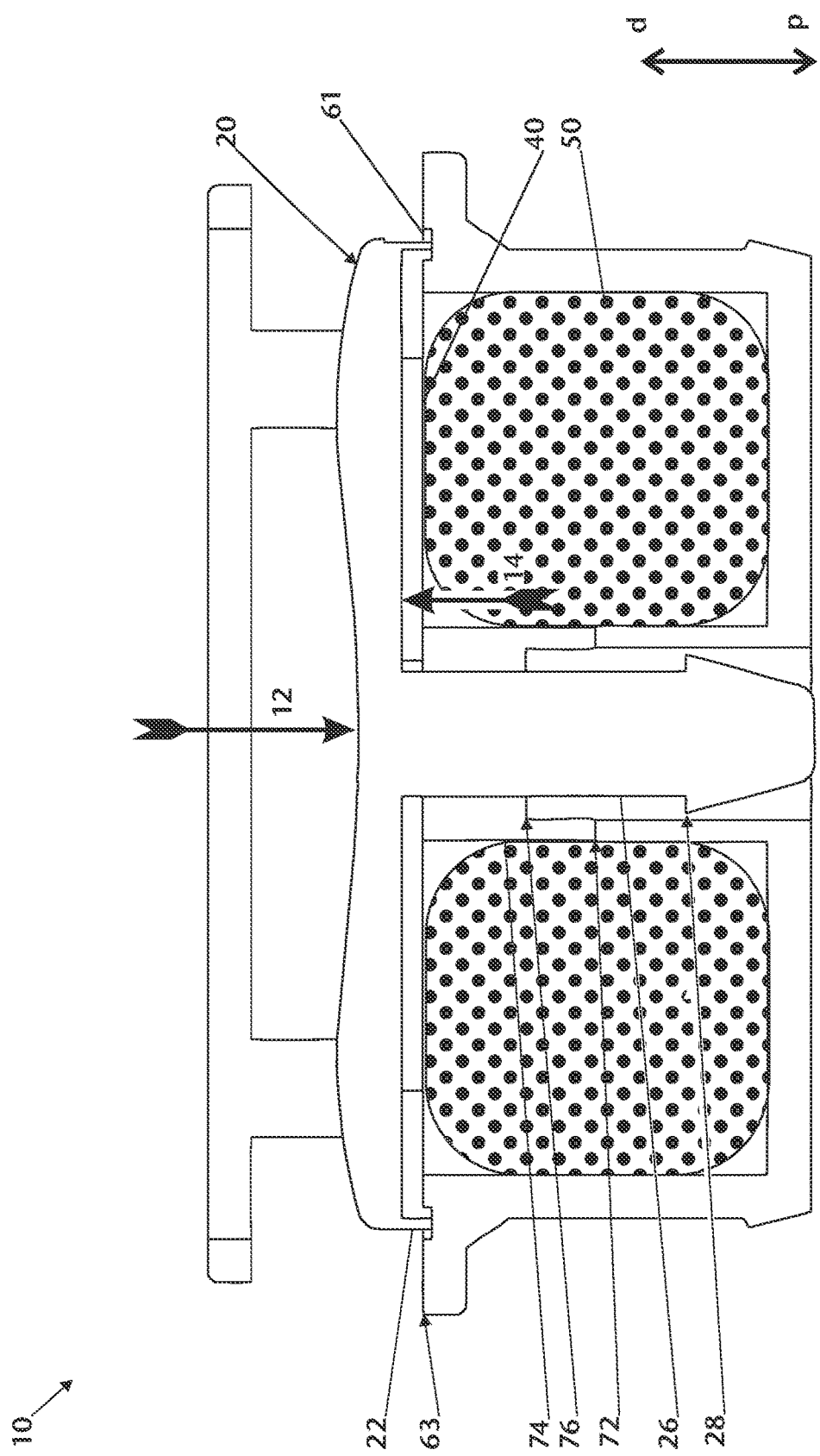
FIG. 3 shows a sectional view of the assembled heat and moisture exchanger shown in FIG. 1, in the closed position.

FIG. 3 shows the heat and moisture exchanger 10 in a closed setting. A closure force 12 in the proximal direction closes the valve plate 20, wherein the lip 22 engages in the groove 61. A return force 14 is exerted on the valve plate 20 by the spring elements 40 that become bowed through the closing of the valve plate 20, which then open the valve plate 20 when the closure force 12 is removed or reduced.

It can also be seen in FIG. 3 that the pin receiver 72 has a latch receiver 74 that is composed of four segments, as can be seen in FIG. 1. A recess 72, in conjunction with the latching projection 26 on the pin 72, prevents the valve plate 20 from sliding or falling out of the pin receiver 72.

The valve plate is centered by the engagement of the lip 22 in the groove 61 in the valve seat 63. The user receives a tactile feedback regarding the closing of the heat and moisture exchanger 10 from the resulting friction. Furthermore, an improved sealing of the heat and moisture exchanger 10 is obtained in the closed setting through the connection of the lip 22 and the groove 61. The filter material 50 is not compressed in this embodiment when it is closed.

Figure 4:
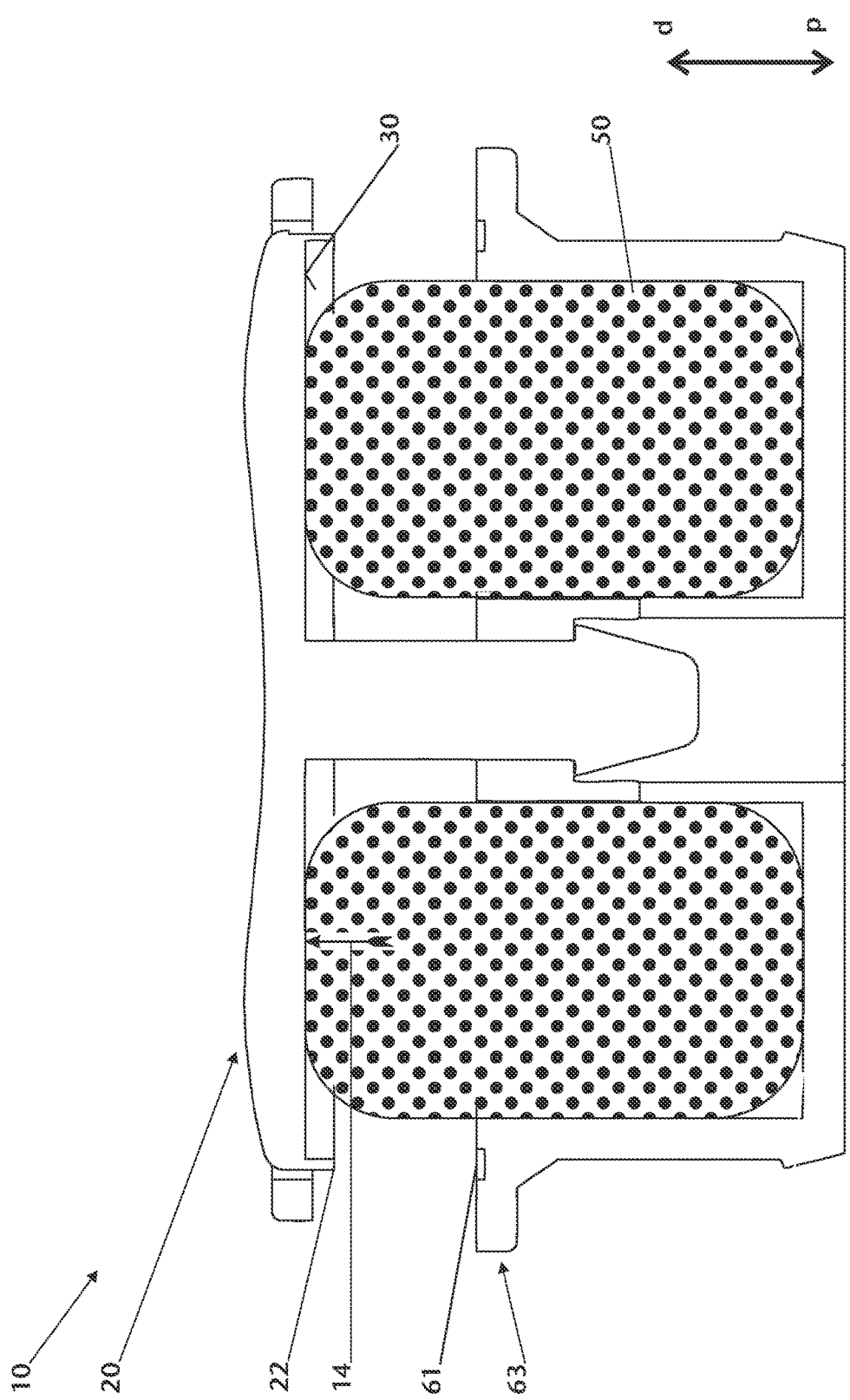
FIG. 4 shows an alternative embodiment of the heat and moisture exchanger.

FIG. 4 shows an alternative embodiment of the heat and moisture exchanger 10, without a spring element. A return force 14 that pushes the valve plate 20 distally into the open setting when the heat and moisture exchanger 10 is closed, not shown herein, is generated by the filter material 50. The filter material 50 extends distally from the respiration guard 70 over the valve seat 63 to the lower surface 30 of the valve plate 20 when it is open.

A further advantage of the seal in the proposed sealing of the heat and moisture exchanger 10 in all of the proposed embodiments is that when closing the valve plate 20, it is centered by the engagement of the lip 22 in the groove 61, and a secure seating of the valve plate 20 on the valve seat 63 is thus ensured.

There is also an embodiment not shown in the figures in which there is no pin 26 and/or pin receiver 72. The return force 14 exerted on the valve plate 20 can be obtained by the filter material 50, as shown in FIG. 4. Furthermore, the valve plate 20 is connected to the filter material 50 by means of adhesive or welding so that the valve plate 20 does not become lost. In another embodiment, the valve plate 20 has projections, not shown in the figures, that engage proximally beneath the frame 64, in order to secure the valve plate 20.

There is also an embodiment not shown in the figures in which the valve plate 20 has a substantially flat distal surface 25. There can also be other contours on the distal surface that are not shown in the figures in various embodiments. Furthermore, there is an embodiment of the respiration guard 70 in the figures, in which it is in the form of a grid, a screen, one or more slats, a perforated plate, a star shape, and/or 3, 5, or more struts. In particular, the struts of the respiration guard can be distributed over the circumference in a uniform or non-uniform manner.

The proposed heat and moisture exchanger provides the tracheotomy or laryngectomy patient with a comfortable possibility for initiating speech, and for receiving a tactile feedback regarding the closure of the heat and moisture exchanger when it is actuated. Furthermore, the placement of the lip in the groove in the closed setting ensures a secure closure of the heat and moisture exchanger. The curvature of the distal upper surface of the valve plate proposed in one embodiment also offers the convenience of being able to press against the center of the valve plate with the finger, in order to exert the closure force in an optimal manner.

The invention claimed is:

1. A heat and moisture exchanger assembly for tracheotomy patients, comprising:
   at least a valve plate and a housing, and
   a spring element associated with the valve plate,
   wherein the valve plate has a radial circumferential lip,
   wherein the housing has a valve seat that surrounds a distal opening of the housing,
   wherein the valve seat has a rim that encircles the housing,
   wherein the valve seat has a groove for receiving the lip,
   wherein the groove is at least partially located in the rim,
   wherein the valve plate is associated with the distal opening of the housing, and
   wherein the valve plate can be closed, such that the lip engages in the groove,
   enabling a laryngectomized or tracheotomized person to speak, when the valve plate is in a closed position,
   wherein the valve plate has a pin that can be inserted into a pin receiver in the housing,
   wherein the spring element includes a central ring for receiving the pin, and
   wherein the central ring has a slot.

2. The heat and moisture exchanger assembly according to claim 1, wherein the groove in the valve seat has a depth that is 10% to 90% of a proximal extension of the lip.

3. The heat and moisture exchanger assembly according to claim 1, wherein the groove has a U-shaped or V-shaped cross section.

4. The heat and moisture exchanger assembly according to claim 1, wherein the valve seat has the rim encircling the housing, wherein the rim has the entire groove.

5. The heat and moisture exchanger assembly according to claim 1, wherein the pin receiver is located in the center of a filter receiver in the housing.

6. A method for closing a heat and moisture exchanger assembly according to claim 1, wherein the valve plate is moved proximally, wherein the lip on the valve plate engages in the groove in the valve seat.

7. The method according to claim 6, wherein the valve plate is moved proximally, counter to a return force exerted by the spring element.

* * * * *